United States Patent
Ben-Zvi et al.

(10) Patent No.: US 10,818,382 B1
(45) Date of Patent: Oct. 27, 2020

(54) SYSTEMS, METHODS, AND APPARATUS FOR ACQUIRING DATA

(71) Applicant: MASSACHUSETTS MUTUAL LIFE INSURANCE COMPANY, Springfield, MA (US)

(72) Inventors: Yaron Ben-Zvi, Hastings on Hudson, NY (US); Gareth Ross, Amherst, MA (US)

(73) Assignee: Massachusetts Mutual Life Insurance Company, Springfield, MA (US)

( * ) Notice: Subject to any disclaimer, the term of this patent is extended or adjusted under 35 U.S.C. 154(b) by 784 days.

(21) Appl. No.: 15/355,708

(22) Filed: Nov. 18, 2016

Related U.S. Application Data

(60) Provisional application No. 62/258,325, filed on Nov. 20, 2015, provisional application No. 62/258,334, filed on Nov. 20, 2015.

(51) Int. Cl.
*G16H 50/30* (2018.01)
*G16H 10/60* (2018.01)

(52) U.S. Cl.
CPC .................................. *G16H 10/60* (2018.01)

(58) Field of Classification Search
CPC ...................................................... G16H 50/30
See application file for complete search history.

(56) References Cited

U.S. PATENT DOCUMENTS

| | | | |
|---|---|---|---|
| 6,314,425 B1 | 11/2001 | Serbinis et al. | |
| 6,422,061 B1 | 7/2002 | Sunshine et al. | |
| 7,310,287 B2 | 12/2007 | Ray et al. | |
| 8,260,489 B2 | 9/2012 | Nielsen et al. | |
| 2002/0077964 A1 | 6/2002 | Brody et al. | |
| 2002/0111835 A1* | 8/2002 | Hele | G06Q 10/10 705/4 |
| 2006/0026051 A1* | 2/2006 | Rose | G06Q 10/10 705/80 |
| 2006/0247968 A1 | 11/2006 | Kadry | |
| 2008/0027752 A1 | 1/2008 | Phan et al. | |
| 2008/0137185 A1* | 6/2008 | Kruczynski | G03B 23/06 359/397 |
| 2009/0019552 A1 | 1/2009 | McLaughlin et al. | |
| 2010/0088752 A1* | 4/2010 | Nagulakonda | H04L 9/3226 726/6 |

* cited by examiner

*Primary Examiner* — John A Pauls
(74) *Attorney, Agent, or Firm* — Foley & Lardner LLP

(57) ABSTRACT

A method comprises receiving a consumer token; in response to the consumer token being associated with the consumer in a consumer profile database, transmitting a first set of questions to the consumer device. The method comprises receiving a session request from the consumer device and generating a session token uniquely identifying a time interval for receipt of consumer data from a physician. The method comprises receiving a physician token; in response to the physician token being associated with the physician token within the session token and a time of receipt being associated with the time interval within the session token, initiating a secure communication session with the physician device and transmitting a second set of questions to the physician device. The method comprises generating a consumer score corresponding to the responses to the first and second plurality of inputs and determining a consumer protection product based on the consumer score.

18 Claims, 5 Drawing Sheets

SYSTEMS, METHODS, AND APPARATUS FOR ACQUIRING DATA

CROSS-REFERENCE TO RELATED APPLICATION

This application claims priority to U.S. Provisional Patent Application Ser. No. 62/258,325, filed on Nov. 20, 2015, and U.S. Provisional Patent Application Ser. No. 62/258,334, filed on Nov. 20, 2015, all of which are hereby incorporated by reference in their entirety.

FIELD OF DISCLOSURE

The present disclosure relates in general to computer-implemented systems, methods, and apparatuses for acquiring data.

BACKGROUND

Many institutions require consumers to undergo medical examinations, which typically involve significant information gathering through a combination of acquiring data from consumers, questions answered during a paramedical exam, several physical measurements and collecting body fluids, and a medical examination by a physician. Traditionally, consumers have been presented an initial questionnaire or phone interviews, which typically ask questions related to lifestyle, health, personal medical history, family medical history, and the like. Usually as a next step in these traditional methods, a non-physician medical professional such as phlebotomist, a nurse practitioner, or a paramedic visits the consumer's home to acquire information by collecting vital statistics, urine sample, blood sample, and/or other invasive or non-invasive bodily fluid or tissue sample(s) to measure one or more bioanalytic parameter of the consumer. However, collecting this data is often a problem for the consumers for a variety of physical and/or psychological reasons, and is often a major barrier to institutions attempting to enroll new consumers. More particularly, the consumers often do not want to have blood drawn at home for fear of needles, do not want to undergo medical screening, do not have the time, and many other reasons.

As the processing power of computers allow for greater computer functionality and the Internet technology era allows for interconnectivity between computing systems, many institutions use computers to acquire consumer information. For example, many of the above-mentioned steps are now performed on computers. However, since the implementation of these more sophisticated tools, several shortcomings in these technologies have been identified and have created a new set of challenges. For example, existing computer-implemented solutions for gathering and managing consumer records suffer from several problems, such as inefficient allocation of system resources to the more informative data and inefficient access to the records from the consumers' physicians. Consumer data may exist on different databases (e.g., motor vehicle records, pharmaceutical records such as prescription drug databases, public records such as Social Security Death Index Master File, and other databases to gather lifestyle, behavior, and other medical and non-medical information). Managing such data on different platforms is difficult due to number, size, content, or relationships of the data associated with the consumers. Moreover, many of the existing software solutions do not provide an efficient method to securely transmit the data. As stated above, one or more steps of the data gathering process will inevitably be performed by a doctor and existing computer-implemented solutions have failed to efficiently verify the work performed and integrate the data with other consumer data from other databases.

SUMMARY

For the aforementioned reasons, there is a need for a more efficient, faster, and secure computer system and method for processing consumer databases, which would allow institutions to profile consumer health in a more efficient manner than possible with human-intervention or conventional computer data-driven analysis. There is a need for a network and computer-specific set of rules to verify physician and other medical test/results associated with the consumer in an efficient and accurate manner. Features disclosed herein allow performing large and complex work such as time-consuming analysis, data-entry tasks, and generating consumer health scores, in a more efficient manner by using less computing power than conventional approaches. Disclosed herein are systems and methods addressing the shortcomings of the art, and may provide any number of additional or alternative advantages.

Certain embodiments disclose a method, which comprises receiving, by a server, a consumer token associated with an electronic consumer device, wherein the consumer token comprises a string of characters uniquely identifying a consumer. The method comprises in response to the consumer token being associated with a first data record of the consumer stored in a consumer profile database, generating by the server, a first graphical user interface comprising a first plurality of questions to be displayed on the electronic consumer device. The method comprises upon transmitting the first graphical user interface to the electronic consumer device, receiving by the server, a first plurality of inputs corresponding to the first plurality of questions. The method comprises receiving, by the server, a session request from the electronic consumer device. The method comprises generating, by the server, a session token comprising a string of characters uniquely identifying a time interval for receipt of data associated with the consumer from a physician. The method comprises generating, by the server, a first instruction configured to display the time interval and data associated with the physician. The method comprises upon transmitting the first instruction to the electronic consumer device, receiving by the server, a physician token associated with an electronic physician device wherein the physician token comprises a string of characters uniquely identifying the physician. The method comprises in response to the received physician token being associated with the physician token within the generated session token and a time of receipt of the physician token being associated with the time interval within the session token, initiating by the server, a secure communication session with the electronic physician device. The method comprises generating, by the server, a second graphical user interface comprising a second plurality of questions to be displayed on the electronic physician device, wherein the second plurality of questions correspond to biological parameters associated with the consumer. The method comprises upon transmitting the second graphical user interface to the electronic physician device, receiving by the server, a second plurality of inputs corresponding to the second plurality of questions. The method comprises generating, by the server, a consumer score corresponding to the first and the second plurality of inputs. The method comprises generating, by the server, a second record of the consumer in the consumer profile database, wherein the second data record is associated to a consumer protection product for the consumer and corresponds to the consumer score. The method comprises generating, by the server, a second instruction configured to display the second data record of the consumer. The method further comprises transmitting, by the server, the instruction to at least one of the electronic consumer device and the electronic physician device.

Another embodiment includes a method for generating a consumer score and a consumer protection product by receiving, by an analytical engine executed by one or more server computers, from a consumer device a plurality of inputs responsive to a plurality of questions, the plurality of inputs provided via a graphical user interface presented at the consumer device, and also receiving from the consumer device a consumer identifier associated with a first record of a consumer stored in a consumer profile database. The method further includes generating, by the analytical engine, a session identifier upon a session request from the consumer device and the receipt of the plurality of inputs from the consumer device, the session identifier being associated with a time interval for receipt of a specimen identifier from a physician device. The method further includes initiating a session upon receipt of a specimen identifier and a physician identifier by the analytical engine from a physician device during the time interval associated with the session identifier; verifying, by the analytical engine, the physician identifier as being associated to a consumer identifier in the first record of the consumer stored in a consumer profile database; and linking, by the analytical engine, the session identifier, the specimen identifier, the physician identifier, and the consumer identifier to continue the session, in response to verification of the physician identifier, and generate a lab order associated with the specimen identifier, the specimen identifier being associated with a physical sample from the consumer and the lab order containing a plurality of instructions for processing the physical sample. The method further includes receiving, by the analytical engine, a first plurality of values for a first plurality of biological parameters associated with the consumer from the physician device and a second plurality of values for a second plurality of biological parameters received after processing the physical sample according to the lab order. The method further includes generating, by the analytical engine, a consumer score for the consumer responsive to the first plurality of values and the second plurality of values; and generating, by the analytical engine, a second record of the consumer in the consumer profile database, the second record associated to a consumer protection product for the consumer and responsive to the consumer score and the plurality of inputs from the consumer device.

In certain embodiments, the method further includes providing a mobile application, by the analytical engine, to be downloaded to the physician device. The mobile application is configured to receive from the physician device the first plurality of values and the second plurality of values and transmit the first plurality of values and the second plurality of values to the consumer profile database.

In certain embodiments, the method further includes providing a web page-based interface, by the analytical engine, on the physician device. The web page-based interface is configured to receive from the physician device the first plurality of values and the second plurality of values and transmit the first plurality of values and the second plurality of values to the consumer profile database.

The physical sample can acquired from the consumer during the time interval associated with the session identifier. The first plurality of values for the first plurality of biological parameters can be transmitted from the physician device during the time interval associated with the session identifier and the second plurality of values for the second plurality of biological parameters can be transmitted from the physician device responsive to processing the physical sample according to the lab order. The first plurality of biological parameters can include one or more biometric parameters. The second plurality of biological parameters can include one or more bioanalytic parameters. The computer-implemented method can further include generating by the analytical engine, on the consumer device a second graphical user interface configured to display the consumer protection product. The consumer protection product can, in an embodiment, be a health product. The plurality of biological parameters can include one or more of bioanalytic parameters and biometric parameters. The bioanalytic parameters can include one or more of qualitative and quantitative measurements of xenobiotics and biotics in tissues and body fluids of the consumer. The biometric parameters can include one or more qualitative and quantitative measurements of physical attributes of the consumer. The physical attributes of the consumer include one or more of DNA, fingerprints, facial features, voice patterns, retinal or iris patterns of the consumer.

In another embodiment, a computer system comprises a server, which is configured to receive a consumer token associated with an electronic consumer device, wherein the consumer token comprises a string of characters uniquely identifying a consumer. The server is configured to in response to the consumer token being associated with a first data record of the consumer stored in a consumer profile database, generate a first graphical user interface comprising a first plurality of questions to be displayed on the electronic consumer device. The server is configured to upon transmitting the first graphical user interface to the electronic consumer device, receive a first plurality of inputs corresponding to the first plurality of questions. The server is configured to receive a session request from the electronic consumer device. The server is configured to generate a session token comprising a string of characters uniquely identifying a time interval for receipt of data associated with the consumer from a physician. The server is configured to generate a first instruction configured to display the time interval and data associated with the physician. The server is configured to upon transmitting the first instruction to the electronic consumer device, receive a physician token associated with an electronic physician device wherein the physician token comprises a string of characters uniquely identifying the physician. The server is configured to in response to the received physician token being associated with the physician token within the generated session token and a time of receipt of the physician token being associated with the time interval within the session token, initiate a secure communication session with the electronic physician device. The server is configured to generate a second graphical user interface comprising a second plurality of questions to be displayed on the electronic physician device, wherein the second plurality of questions correspond to biological parameters associated with the consumer. The server is configured to upon transmitting the second graphical user interface to the electronic physician device, receive a second plurality of inputs corresponding to the second plurality of questions. The server is configured to generate a consumer score corresponding to the first and the second plurality of inputs. The server is configured to generate a second record of the consumer in the consumer profile database, wherein the second data record is associated to a consumer protection product for the consumer and corresponds to the consumer score. The server is configured to generate a second instruction configured to display the second data record of the consumer. The server is further configured to transmit the instruction to at least one of the electronic consumer device and the electronic physician device.

The processing unit can be further configured to execute a set of instructions to provide a mobile application, by the analytical engine, to be downloaded to the physician device. The mobile application is configured to receive from the physician device the first plurality of values and the second plurality of values and transmit the first plurality of values and the second plurality of values to the consumer profile database.

The processing unit can be further configured to execute a set of instructions to provide a web page-based interface, by the analytical engine, on the physician device. The web page-based interface is configured to receive from the physician device the first plurality of values and the second plurality of values and transmit the first plurality of values and the second plurality of values to the consumer profile database.

The processing unit can be further configured to execute a set of instructions to generate, by the analytical engine, on the consumer device a second graphical user interface configured to display the consumer protection product.

Numerous other aspects, features and benefits of the present disclosure may be made apparent from the following detailed description taken together with the drawing figures. The systems can include less components, more components, or different components depending on desired analysis goals. It should be further understood that both the foregoing general description and the following detailed description are exemplary and explanatory and are intended to provide further explanation of the invention as claimed.

BRIEF DESCRIPTION OF THE DRAWINGS

The present disclosure can be better understood by referring to the following figures. The components in the figures are not necessarily to scale. The emphasis is instead placed upon illustrating the principles of the disclosure. In the figures, reference numerals designate corresponding parts throughout the different views.

DETAILED DESCRIPTION

Figure 1:
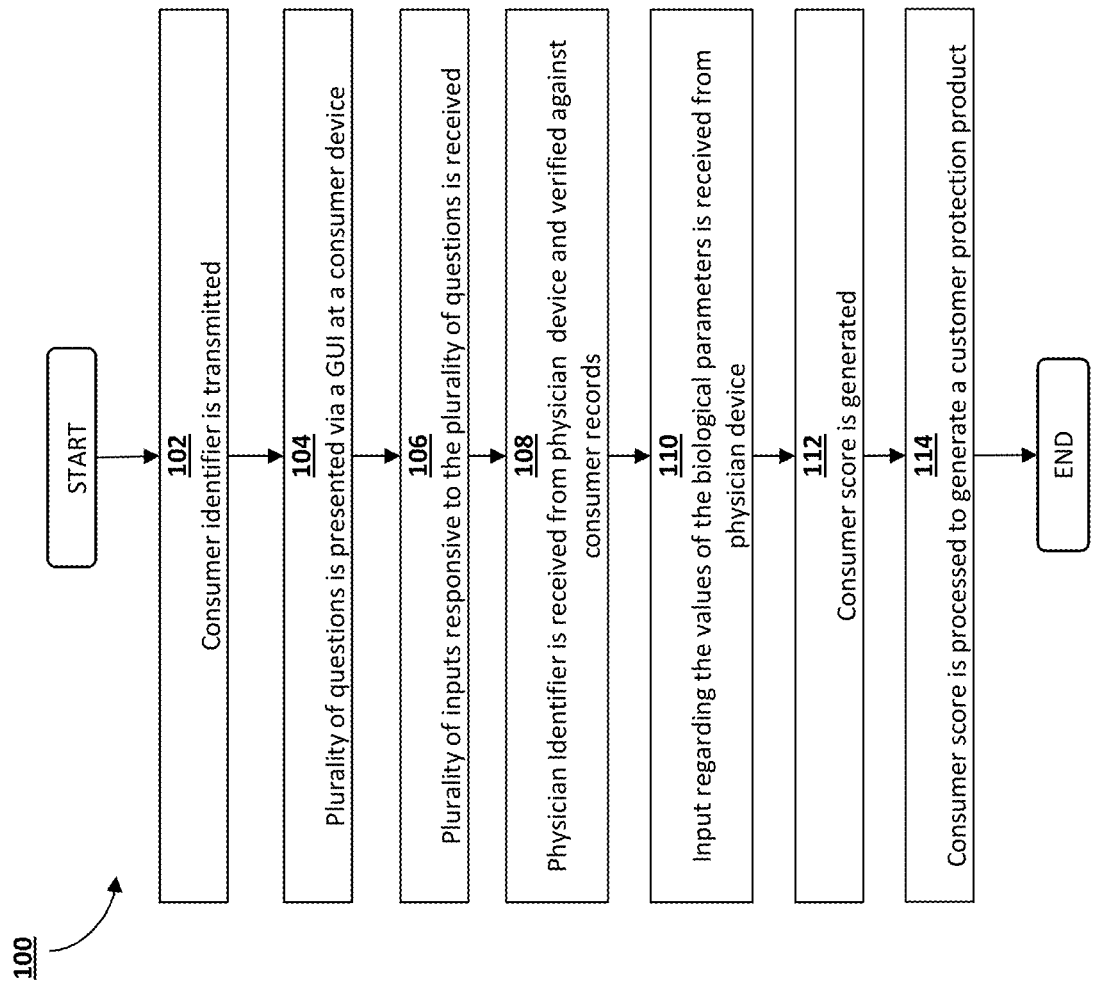
FIG. 1 is flowchart of a method for acquiring information for consumer assessment of a consumer, according to an embodiment.

Reference will now be made to the exemplary embodiments illustrated in the drawings, and specific language will be used here to describe the same. It will nevertheless be understood that no limitation of the scope of the invention is thereby intended. Alterations and further modifications of the inventive features illustrated here, and additional applications of the principles of the inventions as illustrated here, which would occur to one skilled in the relevant art and having possession of this disclosure, are to be considered within the scope of the invention.

As used here, the following terms may have the following definitions:

"Price" refers to a periodic payment that a consumer offers to a financial institution or a health-related consumer protection company.

"Scoring process" refers to the health assessment of a consumer. It quantifies the health that an institution may accept in exchange for the payment of a price.

"Agent" refers to an individual working for a company or as a broker with an interest in attracting new consumers by analyzing their needs and wishes for protecting against health-related problems. An agent may specifically look for consumers with high referral potential. In addition, an agent may represent the intermediary between an issuing company and a consumer.

"Analytical engine" refers to a server comprising a software module that handles data integration, breaks data streams into atomic parts, executes rules, and performs data matching by using fuzzy logic, among others.

"Biological parameter" refers to one of the many bioanalytic, biometric, or other measurable biological attributes of an individual that are used to evaluate a consumer during the consumer assessment process. "Bioanalytics," as used herein, refers to qualitative, quantitative, or a combination of both types of measurement of xenobiotics (drugs and their metabolites, and biological molecules in unnatural locations or concentrations) and biotics (macromolecules, proteins, DNA, large molecule drugs, metabolites) in tissues and body fluids of the consumer. "Biometrics," as used herein, refers to qualitative and quantitative measurements and analysis of physical attributes of the consumer, including but not limited to height, weight, DNA, fingerprints, facial features, voice patterns, retinal or iris patterns, and such. Examples of biological parameters include blood pressure, heart rate, and levels of drugs, cells, ions, and metabolites in the blood, urine, stools, hair, sweat, and other physical samples.

"Consumer score," as used herein, refers to a value obtained through actuarial evaluation and analysis of the information associated to a particular consumer in a consumer profile database such as health-related data. "Consumer protection products and services," as used herein, include financial products and professional services that manage or control health-related or other problems, and respond and compensate for property and human loss, damage, and casualty. Consumer protection products, for example, without limitations, may include health-related products.

"Values for the biological parameters," as used herein, refers to historical and current values of biological parameters associated with a consumer, as provided by bioanalytics, biometrics, and other analysis and measurements. Examples of values of biological parameters include a systolic/diastolic blood pressure value (e.g., 110/75), a weight measurement (e.g., 160 lbs.), a heart rate measurement (e.g., 70 beats a minute), a total serum iron concentration (e.g., 100 μmol/L), and a triglyceride level (e.g., 75 mg/dL), among other biometric and bioanalytical measurements that would be understood by one of ordinary skill in the art.

An attending physician statement is the standard way to obtain comprehensive information regarding a consumer, but is the more expensive and time consuming component of a consumer assessment system. The consumer's physician can provide a complete perspective, including all medical diagnosis regarding the consumer and associated treatment, as well as any laboratory test results. More suitable consumer protection products can be better developed when the ways to acquire consumer's biological information, such as bioanalytics, biometrics, and other measurements are streamlined. The consumer's records can be supplemented with aggregated data from databases such as the motor vehicle records, pharmaceutical records such as prescription drug databases, public records such as Social Security Death Index Master File, and other databases for consumer assessment processes. Currently, this aggregated data from external sources is cross-checked against the data acquired from the analysis of the body fluids collected from the consumer. This addresses fraud associated with collection of fluids by non-physician medical professional, but does not necessarily cutout the use of non-physician medical professionals. Fluid collection kits acquired from the consumer by the non-physician medical professionals still need to be processed by the consumer assessment company such as a vendor or provider of other financial or health-related products. And there are limits to non-physician medical professionals' activity of collection of fluids and inquiries regarding health history, and online collection of health history.

Certain embodiments of the invention include software for consumer assessment companies that allow a potential consumer, during the process of purchase of consumer protection products and services, to go directly to his doctor or physician for his medical records. This eliminates the need for a non-physician medical professional, such as a paramedic or phlebotomist to go to that person's home to take blood, and is more efficient in expenditure of time, money, and human resources. Disclosed herein are systems to facilitate the acquisition of biological information about the consumer directly from his physician, and software applications and graphical user interfaces used by the physician or the consumer to communicate the biological information to the consumer assessment company. The biological information includes historical and current values of the biological parameters, as provided by bioanalytics, biometrics, and other analysis and measurements.

Certain embodiments of the method include receiving, by an analytical engine executed by one or more server computers, from a consumer device a plurality of inputs responsive to a plurality of questions. The plurality of inputs is provided via a graphical user interface presented at the consumer device. The analytical engine also receives from the consumer device a consumer identifier associated with a first record of a consumer stored in a consumer profile database. In the next step, the analytical engine verifies a physician identifier from a physician device as being associated to the consumer identifier in the first record of the consumer stored in a consumer profile database. In the next step, the analytical engine receives from a physician device a plurality of values for a plurality of biological parameters associated with the consumer and stored in the consumer profile database, in response to verification of the physician identifier as being associated to the consumer identifier in the first record of the consumer stored in a consumer profile database. In the next step, the analytical engine generates a consumer score for the consumer responsive to the plurality of values for the plurality of biological parameters received from the physician device. In the next step, the analytical engine generates a second record of the consumer in the consumer profile database. This second record is associated to a consumer protection product for the consumer and is responsive to the consumer score and the plurality of inputs from the consumer device. The consumer identifier can be uniquely associated to the consumer device and the consumer. The physician identifier can be further associated to the physician device and is generated in response to the plurality of inputs provided via a graphical user interface presented at the consumer device. The computer-implemented method can further include providing a mobile application, by the analytical engine, to be downloaded to the physician device. This mobile application is configured to receive from the physician device the plurality of values for the plurality of biological parameters associated with the consumer and transmit the plurality of values for the plurality of biological parameters associated with the consumer to the consumer profile database. The computer-implemented method can further include generating by the analytical engine, on the consumer device a second graphical user interface configured to display the consumer protection product. The plurality of biological parameters can include one or more of bioanalytic parameters and biometric parameters. The bioanalytic parameters can include one or more of qualitative and quantitative measurements of xenobiotics and biotics in tissues and body fluids of the consumer. The biometric parameters can include one or more qualitative and quantitative measurements of physical attributes of the consumer. The physical attributes of the consumer include one or more of DNA, fingerprints, facial features, voice patterns, retinal or iris patterns of the consumer.

Another embodiment includes a method for generating a consumer score and a consumer protection product by receiving, by an analytical engine executed by one or more server computers, from a consumer device a plurality of inputs responsive to a plurality of questions, the plurality of inputs provided via a graphical user interface presented at the consumer device, and also receiving from the consumer device a consumer identifier associated with a first record of a consumer stored in a consumer profile database. In the next step, the analytical engine generates a session identifier upon a session request from the consumer device and the receipt of the plurality of inputs from the consumer device, the session identifier being associated with a time interval for receipt of a specimen identifier from a physician device. In the next step, the analytical engine initiates a session upon receipt of a specimen identifier and a physician identifier by the analytical engine from a physician device during the time interval associated with the session identifier and verifies the physician identifier as being associated to a consumer identifier in the first record of the consumer stored in a consumer profile database. In the next step, the analytical engine links the session identifier, the specimen identifier, the physician identifier, and the consumer identifier to continue the session, in response to verification of the physician identifier. In the next step, the analytical engine generates a lab order associated with the specimen identifier. The specimen identifier is associated with a physical sample from the consumer and the lab order contains a plurality of instructions for processing the physical sample. In the next step, the analytical engine receives a first plurality of values for a first plurality of biological parameters associated with the consumer from the physician device and a second plurality of values for a second plurality of biological parameters received after processing the physical sample according to the lab order. In the next step, the analytical engine generates a consumer score for the consumer responsive to the first plurality of values and the second plurality of values; and further generates a second record of the consumer in the consumer profile database. The second record is associated to a consumer product for the consumer and responsive to the consumer score and the plurality of inputs from the consumer device.

In certain embodiments, the method further includes providing a mobile application, by the analytical engine, to be downloaded to the physician device. The mobile application is configured to receive from the physician device the first plurality of values and the second plurality of values and transmit the first plurality of values and the second plurality of values to the consumer profile database.

In certain embodiments, the method further includes providing a web page-based interface, by the analytical engine, on the physician device. The web page-based interface is configured to receive from the physician device the first plurality of values and the second plurality of values and transmit the first plurality of values and the second plurality of values to the consumer profile database.

The physical sample can acquired from the consumer during the time interval associated with the session identifier. The first plurality of values for the first plurality of biological parameters can be transmitted from the physician device during the time interval associated with the session identifier and the second plurality of values for the second plurality of biological parameters can be transmitted from the physician device responsive to processing the physical sample according to the lab order. The first plurality of biological parameters can include one or more biometric parameters. The second plurality of biological parameters can include one or more bioanalytic parameters. The computer-implemented method can further include generating by the analytical engine, on the consumer device a second graphical user interface configured to display the consumer protection product. The plurality of biological parameters can include one or more of bioanalytic parameters and biometric parameters. The bioanalytic parameters can include one or more of qualitative and quantitative measurements of xenobiotics and biotics in tissues and body fluids of the consumer. The biometric parameters can include one or more qualitative and quantitative measurements of physical attributes of the consumer. The physical attributes of the consumer include one or more of DNA, fingerprints, facial features, voice patterns, retinal or iris patterns of the consumer.

FIG. 1 is a flowchart showing an exemplary process 100 for acquiring information associated with a consumer. In a first step 102, an analytical engine receives, from the consumer device, a consumer identifier associated with a first record of a consumer stored in a consumer profile database. The consumer identifier can be received either at the beginning of the interaction with the consumer assessment system or after a certain amount of information is received from the consumer. In other aspects, the consumer identifier can also be generated by the analytical engine in response to certain information records and provided to the consumer device. The consumer device can then transmit this identifier as part of the authentication protocols for the interaction.

In a next step 104, the analytical engine executed by one or more server computers presents a plurality of questions to a consumer via a graphical user interface (GUI) at a consumer device. In some embodiments, the analytical engine may generate an instruction and transmit said instruction to the computing device to display the GUI. In a next step 106, the analytics engine receives a plurality of inputs, from the GUI, responsive to the plurality of questions. Responsive to this plurality of inputs, the analytical engine generates a physician identifier and provides this identifier to a physician device. The analytical engine generates a session identifier, which provides a time interval for information to be received from the physician device. In another aspect, the physician identifier can be generated when the consumer's physician downloads a mobile application and provides a consumer identifier or other information associated to the consumer as part of the login process.

Upon a session request from the consumer, a session identifier is generated by the analytical engine, which provides a time interval for information to be received from the physician device. For example, this time interval can be a particular appointment time scheduled between the consumer and the doctor. This time interval can be the next available appointment time for the doctor. When the physician evaluates a consumer during the time interval associated to the session, the analytical engine verifies a physician identifier from a physician device as being associated to the consumer identifier in the first record of the consumer stored in a consumer profile database, as shown in the next step 108. When the physician evaluates a consumer during the time interval associated to the session, the analytical engine links the session identifier, the specimen identifier, the physician identifier, and the consumer identifier to continue the session, in response to verification of the physician identifier, and generates a lab order associated with the specimen identifier, the specimen identifier being associated with a physical sample from the consumer and the lab order containing a plurality of instructions for processing the physical sample. In the next step 110, the analytical engine receives, from a physician device, a plurality of values for a plurality of biological parameters associated with the consumer and stored in the consumer profile database. The plurality of biological parameters can be evaluated at the physician's office or at a lab using a lab order with instructions regarding processing of the physical samples.

In the next step 112, the analytical engine generates a consumer score for the consumer responsive to the plurality of values for the plurality of biological parameters received from the physician device. In the next step 114, the analytical engine processes the consumer score to generate a second record of the consumer in the consumer profile database. This second record is associated to a consumer protection product for the consumer and is responsive to the consumer score and the plurality of inputs from the consumer device. This consumer protection product can be further presented to the consumer, and purchasing decisions can be explored.

Figure 2A:
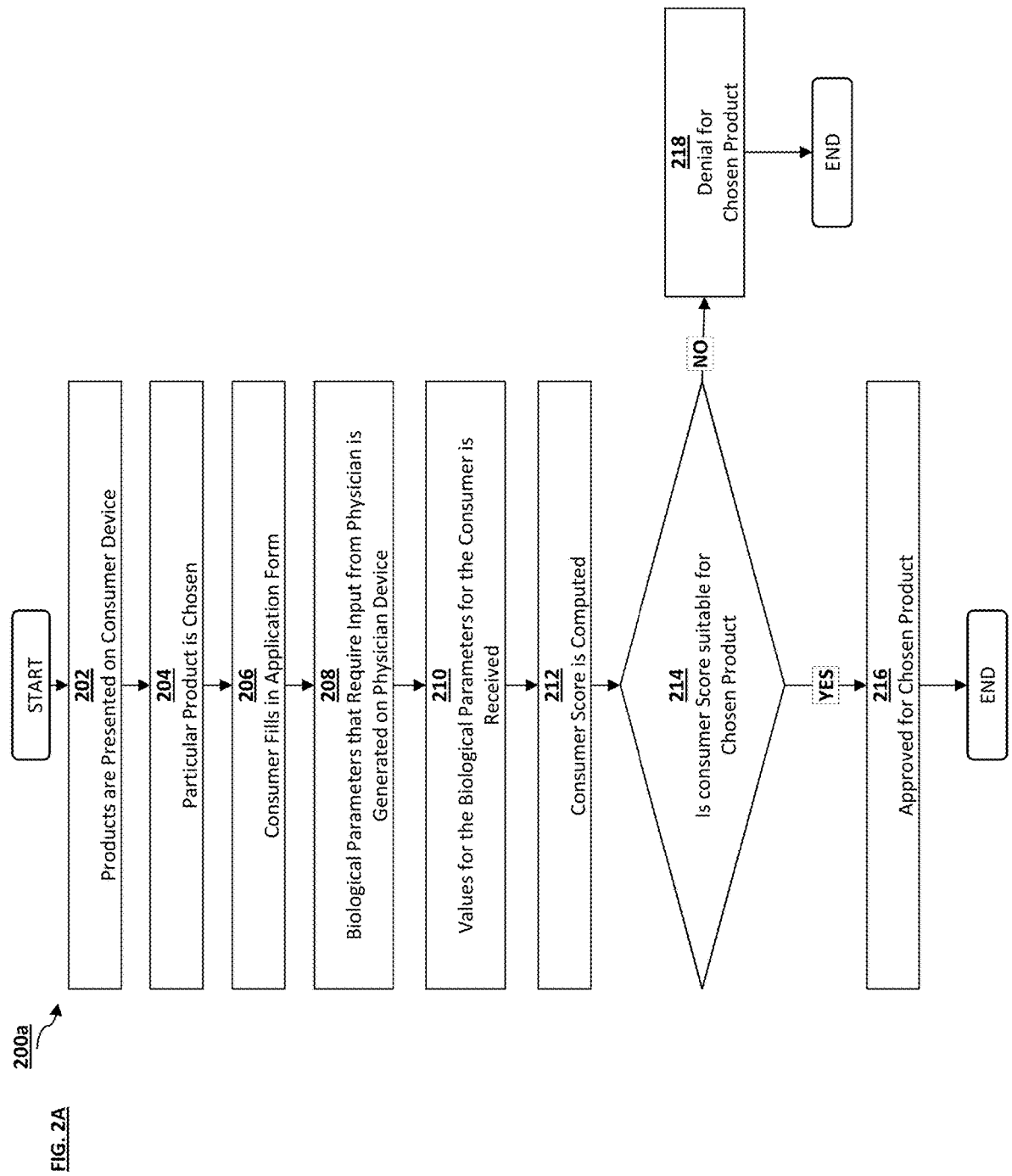
FIGS. 2A and 2B are flowcharts of methods for acquiring information for consumer assessment of a consumer, according to an embodiment.

FIG. 2A is a flowchart showing an exemplary process 200a for acquiring information associated with a consumer by the analytical engine. In a first step 202, an electronic interface displaying a suite of consumer protection products is presented to a consumer device by an analytical engine associated with a client. The consumer is presented on his device with a menu of options regarding the type of consumer protection products available, the criteria for evaluating the consumer associated with each of the consumer protection product, financial information such as price and value associated with each of the consumer protection product, and other such information as known in the art to be important to choosing and providing consumer protection products and services.

In the next step 204, the consumer chooses (e.g., the analytical engine receives from the user interface) a particular consumer protection product. The consumer is then presented, by the analytical engine, with a plurality of questions to determine his eligibility for the consumer protection product. Here, the consumer can be presented with questions geared to evaluate his eligibility and then proceeds in step 206 to provide the information required to evaluate his eligibility for a particular consumer protection product. The consumer can input his information by filling an application form or responding to other data collection mechanisms. This interaction can take the form of a fixed questionnaire, a chat, virtual interview, or other data collection interfaces.

Upon a session request from the consumer, a session identifier is generated by the analytical engine, which provides a time interval for information to be received from the physician device. For example, this time interval can be a particular appointment time scheduled between the consumer and the doctor. This time interval can be the next available appointment time for the doctor. When the physician evaluates a consumer during the time interval associated to the session, the analytical engine verifies a physician identifier from a physician device as being associated to the consumer identifier in the first record of the consumer stored in a consumer profile database. When the physician evaluates a consumer during the time interval associated to the session, the analytical engine links the session identifier, the specimen identifier, the physician identifier, and the consumer identifier to continue the session, in response to verification of the physician identifier, and generate a lab order associated with the specimen identifier, the specimen identifier being associated with a physical sample from the consumer and the lab order containing a plurality of instructions for processing the physical sample. In a next step 208, the analytical engine of the consumer company generates a web-based or an app-based display on the physician device (e.g., instructs the device to display) that presents the list of biological parameters to be evaluated by the consumer's physician or requires input from the consumer's physician. In other aspects, this display can also be presented on a consumer device. This display can be in the form of a fillable form or other data collection interfaces or can be configured to receive information regarding the biological parameters directly from another device or database from the physician's office.

In a next step 210, the analytical engine receives input regarding the values of the biological parameters for the consumer and is stored as part of the consumer records in the consumer profile database. The information regarding the biological parameters can be inputted when the consumer visits his physician's office for an annual examination, or can be provided by the physician from records of the consumer.

In a next step 212, the analytical engine computes a consumer score for the consumer based on information acquired from a variety of sources, including the consumer's application, public databases, and information acquired from the physician regarding the values of the biological parameters. In a next step 214, the particular consumer protection product chosen by the consumer is evaluated, by the analytical engine, for actuarial suitability to the computed consumer assessment score. If the particular consumer protection product is actuarially suitable to the computed consumer score (e.g., does satisfy a pre-determined score threshold), as in step 216, then that particular consumer protection product is approved, by the analytical engine, for the consumer. If the particular consumer protection product is actuarially not suitable to the computed consumer score (e.g., does not satisfy a pre-determined score threshold), as in step 218, then that particular consumer protection product is denied to the consumer. In certain embodiments, the consumer can then be presented with a different specification and attributes to better serve the consumer. Therefore, this consumer protection product has been provided to a consumer without the consumer protection company having to send a non-physician medical professional, such as phlebotomists and paramedics, to visit the consumer and collect bodily fluids. As one would understand, non-physician medical professionals are the medical professionals who are sent on behalf of the consumer protection company to collect samples and gather information from the consumer. These non-physician medical professionals are not instructed by the physician to collect fluids or other information regarding the biological parameters. This term as used herein does not refer to medical professionals who work in the physician's office, or who collect fluids or other information on behalf of the physician regarding the biological parameters of the consumer.

In certain embodiments, providing consumer protection products and services electronically involves a web-based system that receives a person's whole medical history directly from the physician or the consumer, instead using an independent non-physician medical professional. The physicians can send the biological information regarding the consumer directly to the web-based system, as they are already gathering this information. Provided in some embodiments is an electronic interface for the doctor to submit the biological information regarding the consumer, including his evaluation of the values of the biological parameters. This electronic interface can be accessed from any device available to the physician. In certain embodiments, the analytical engine through an electronic interface provides for automated submission of invoices for services performed by the physician, communication of subsequent approval of invoices, and payment to the physician for his services. The consumer, who is a patient of the physician, can also show up with a device displaying an electronic interface. For example, the patient can show up with an app on his smartphone that the doctor may use to input the biological information required by the consumer protection company.

Figure 2B:
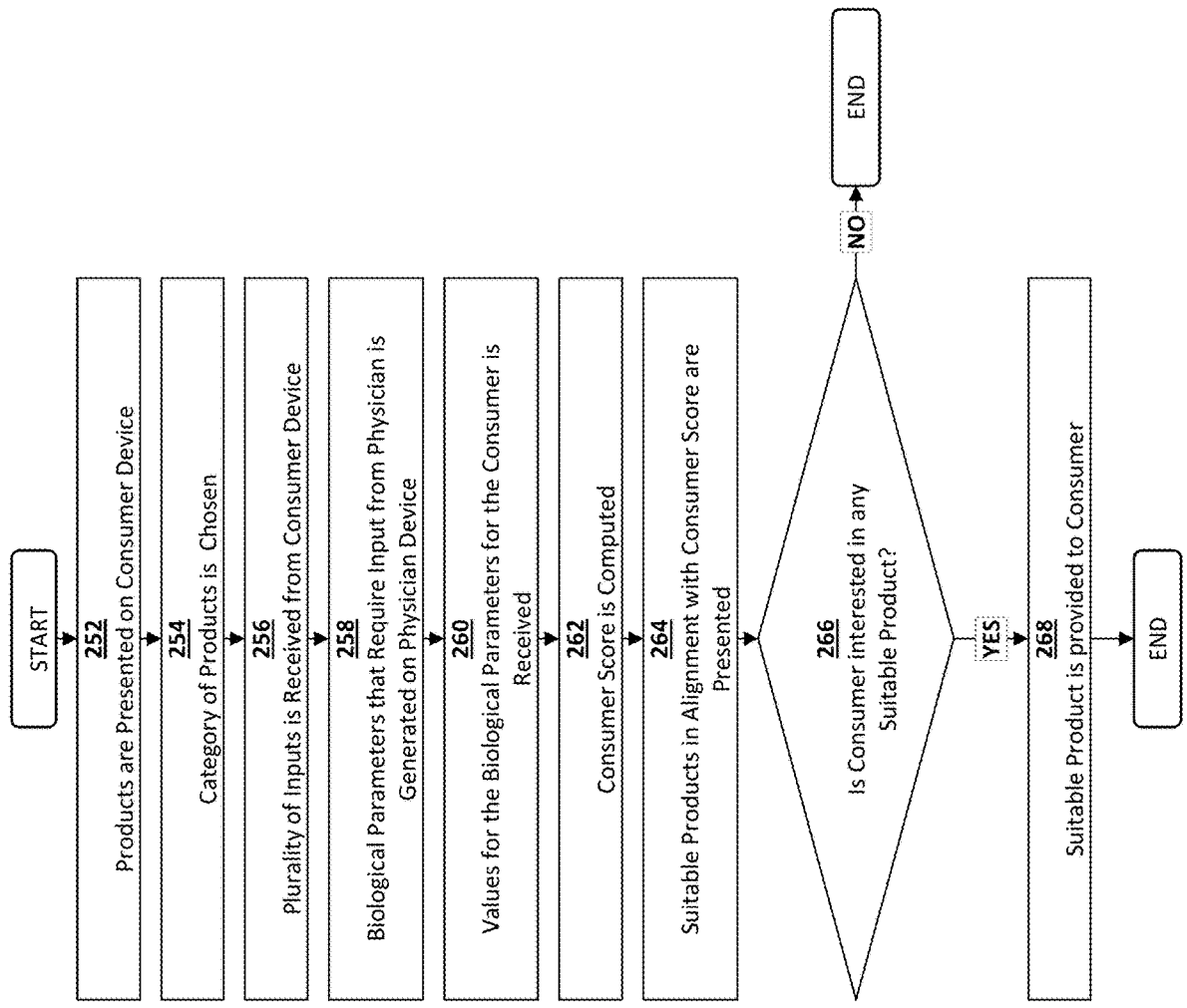

FIG. 2B is a flowchart showing an exemplary process 200a for acquiring information associated with a consumer. In a first step 252, an electronic interface displaying a suite of consumer protection products is presented to a consumer on a consumer device by an analytical engine of a consumer protection system. The consumer is presented with a menu of options regarding the type of consumer protection products available. For example, a consumer who is shopping for health-related product is presented with different categories of health-related product, such as term life, whole life, guarantee universal life, index universal life, and other such products as known in the art. In the next step 254, the consumer chooses (e.g., the analytical engine receives an input from the consumer) a particular category of consumer protection product, and then proceeds in step 256 to provide the information required to present suitable consumer protection products. The consumer can input his information by filling an application form or responding to other data collection mechanisms. This interaction can take the form of a fixed questionnaire, a chat, virtual interview, or other data collection interfaces.

In a next step 258, the analytical engine of the consumer protection company generates a web-based or an app-based display that presents the list of biological parameters to be evaluated by the consumer's physician or requires input from the consumer's physician. This display can be presented on a consumer device or a physician device. This display can be in the form of a fillable form or can be configured to receive information regarding the biological parameters directly from another device or database from the physician's office.

In a next step 260, the analytical engine acquires input regarding the values of the biological parameters for the consumer from the consumer device or physician device. The information regarding the biological parameters can be inputted (in the consumer device or the physician device) when the consumer visits his physician's office for an annual examination, or can be provided by the physician from records of the consumer. In a next step 262, the analytical engine computes a consumer score for the consumer based on information acquired from a variety of sources, including the consumer's application, public databases, and information acquired from the physician regarding the values of the biological parameters. In some embodiments, the analytical engine may generate an instruction and transmit said instruction to a database and query information needed from the database.

In a next step 264, the consumer is presented, by the analytical engine, with suitable consumer protection products that are actuarially responsive to the computed consumer score. The consumer, as in step 266, is presented with a choice to proceed acquiring one of the presented consumer protection products. The consumer, as in step 268, can proceed to acquire a consumer protection product that meets his needs. If the presented consumer protection products are not suitable for his needs or if he does not like the financial constraints, he can end the purchasing process or explore other products. In certain embodiments, the consumer can then be presented with a different product such as a consumer protection product with lower coverage than initially presented, or one with higher cost and desired coverage. Therefore, this consumer protection product has been provided to a consumer without the consumer protection company utilizing information gathered by a non-physician medical professional, such as phlebotomists and paramedics, during a visit to the consumer's home or office. The changes to the consumer assessment process here include more than the use of web-based applications and attending physician statements (APS). Embodiments of the invention may not involve the use of paramedical exams, home visits, and embarrassing or sensitive medical questions during follow-ups.

One or more of the information records associated to a consumer can be used to generate a consumer identifier that is uniquely associated with the consumer, the consumer device, or both. A consumer identifier as used herein can be any image, token, code or string of characters including a plurality of letters, numbers, or symbols, or other means of uniquely identifying the consumer, the consumer device, or both. One or more of the information records associated to a consumer can be used to generate a physician identifier. A physician identifier as used herein can be any image, token, code or string of characters including a plurality of letters, numbers, or symbols, or other means of uniquely identifying the physician, or the physician device, or both. In certain embodiments, the physician identifier can be associated to the physician device and is generated in response to the plurality of inputs provided via a graphical user interface presented at the consumer device. For example, the consumer can provide the name of his doctor, or the clinic. The system (e.g., the analytical engine) then generates a unique identifier that is provided to the physician device, and stored as part of the information records for a particular patient/consumer in the consumer profile database. In certain embodiments, a physician can have five different physician identifiers, each uniquely associated to the information for a particular patient/consumer in the consumer profile database. The physician device can be associated to all five physician identifiers. Each physician identifier is associated with a particular consumer identifier. In another example, a physician can login with a unique physician identifier on a physician device, and then proceed to upload records associated to several patients into the consumer profile database. The physician identifier is verified as being associated with a consumer identifier, generated from one or more of the information records associated to a consumer. These records include identifiers such as name or other patient identification that link the individual records from the physician to a particular patient/consumer in the consumer profile database. In each case, only an authorized physician device can provide records to the consumer profile database.

In certain embodiments of the method, when the consumer fills in an application for a consumer protection product, the analytical engine generates a session identifier. A session identifier as used herein can be any image, token, code or string of characters including a plurality of letters, numbers, or symbols, or other means of identifying a session wherein the consumer is scheduled to meet with his physician for an assessment of a plurality of biological parameters associated with the consumer. For example, the session identifier is associated with a time interval during which the consumer visits his physician and provides a physical sample for further analysis. The session identifier is configured to be valid only during the time interval, and expires at the end of the time interval. The session identifier can be configured to any pre-determined time interval or chosen by the consumer, such as a three-hour window, an eight-hour window, or a two-day window. If the consumer cannot make it to a session, then he resubmits a request to the system. This resets the session identifier and generates a new time interval, and the consumer visits his physician during the new time interval.

A specimen identifier as used herein can be any image, token, code or string of characters including a plurality of letters, numbers, or symbols, or other means of identifying a physical sample associated with a consumer. The specimen identifier can be a QR code or a unique image. In an embodiment, the containers with the specimen identifiers for the collection of the physical samples can be sent to the consumer before the session with his physician. In other embodiments, the containers with the specimen identifiers for the collection of the physical samples can be sent to the physician before the session with the consumer. In other embodiments, standard containers for the collection of the physical samples are used, and the physician or other professionals who work at the physician's office can generate a label with the specimen identifier in preparation for or during a session with a consumer.

In certain embodiments, when the consumer visits the physician's office during the time interval associated with the session identifier, the physician scans containers with specimen identifiers such as bar codes and correlates the specimen identifiers with physical samples acquired from the consumer. When the analytical engine verifies the physician identifier, it links the session identifier, the specimen identifier, the physician identifier, and the consumer identifier to continue the session and generate a lab order with instructions for processing the physical samples. Thus, the lab order is authenticated by the physician's office.

The physician can also initiate a session with the consumer assessment system, and provide a session identifier to the consumer depending on the physician's availability for conducting an assessment of the consumer. Only during the appointment session, the session identifier can be linked to the consumer identifier, the physician identifier and the specimen identifier. The entire session can be executed using the consumer device in contact with the consumer assessment system, or using the physician device in contact with the consumer assessment system, or a combination thereof. Certain biological parameters associated with the consumer can be evaluated during the appointment session in the physician's office. For example, these biological parameters can include certain biometric parameters such as height, weight, facial features, voice patterns, retinal or iris patterns, and such. Other biological parameters that can be evaluated at the physician's office include blood pressure, heart rate, and levels of drugs, cells, ions, and metabolites in the blood, urine, stools, hair, sweat, and other physical samples. These physical samples can also be sent to a lab pursuant to a lab order for evaluation of certain biological parameters such as the presence of xenobiotics and biotics. The analytical engine generates a consumer score for the consumer responsive to the values for the biological parameters that may be stored in the consumer profile database. The analytical engine generates a second record that is associated to a consumer protection product for the consumer, which is based on the consumer score and the plurality of inputs from the consumer device.

In certain embodiments, a mobile application can be provided, to the physician device. The mobile application, in direct communication with the analytical engine, is configured to receive from the physician device the specimen identifier, the session identifier, the consumer identifier, and the values for the biological parameters associated with the consumer, and transmit these values to the consumer profile database. In certain embodiments, a web page-based interface can be provided to the physician device. The web page-based interface is configured to receive from the physician device the specimen identifier, the session identifier, the consumer identifier, and the values for the biological parameters associated with the consumer, and transmit these values to the consumer profile database.

Certain embodiments include a system for generating a consumer score and a consumer protection product. This system includes a non-transitory memory; one or more server computers; and a processing unit in communication with said non-transitory memory, and configured to execute a set of instructions. The processing unit is configured to execute a set of instructions to receive from a consumer device a plurality of inputs responsive to a plurality of questions presented at the consumer device; receive from the consumer device a consumer identifier associated with a first record of a consumer stored in a consumer profile database; generate a session identifier upon a session request from the consumer device and the receipt of the plurality of inputs from the consumer device, the session identifier being associated with a time interval for receipt of a specimen identifier from a physician device; initiate a session upon receipt of a specimen identifier and a physician identifier at the analytical engine sent from a physician device during the time interval associated with the session identifier; verify the physician identifier as being associated to a consumer identifier in the first record of the consumer stored in a consumer profile database; link the session identifier, the specimen identifier, the physician identifier, and the consumer identifier to continue the session, in response to verification of the physician identifier, and generate a lab order associated with the specimen identifier, the specimen identifier being associated with a physical sample from the consumer and the lab order containing a plurality of instructions for processing the physical sample; receive a first plurality of values for a first plurality of biological parameters associated with the consumer from the physician device and a second plurality of values for a second plurality of biological parameters received after processing the physical sample according to the lab order; generate a consumer score for the consumer responsive to the first plurality of values and the second plurality of values; and generate a second record of the consumer in the consumer profile database. The second record is associated to a consumer protection product for the consumer and is responsive to the consumer score and the plurality of inputs from the consumer device.

The processing unit can be further configured to execute a set of instructions to provide a mobile application, by the analytical engine, to be downloaded to the physician device. The mobile application is configured to receive from the physician device the first plurality of values and the second plurality of values and transmit the first plurality of values and the second plurality of values to the consumer profile database.

The processing unit can be further configured to execute a set of instructions to provide a web page-based interface, by the analytical engine, on the physician device. The web page-based interface is configured to receive from the physician device the first plurality of values and the second plurality of values and transmit the first plurality of values and the second plurality of values to the consumer profile database.

The processing unit can be further configured to execute a set of instructions to generate, by the analytical engine, on the consumer device a second graphical user interface configured to display the consumer protection product.

Figure 3:
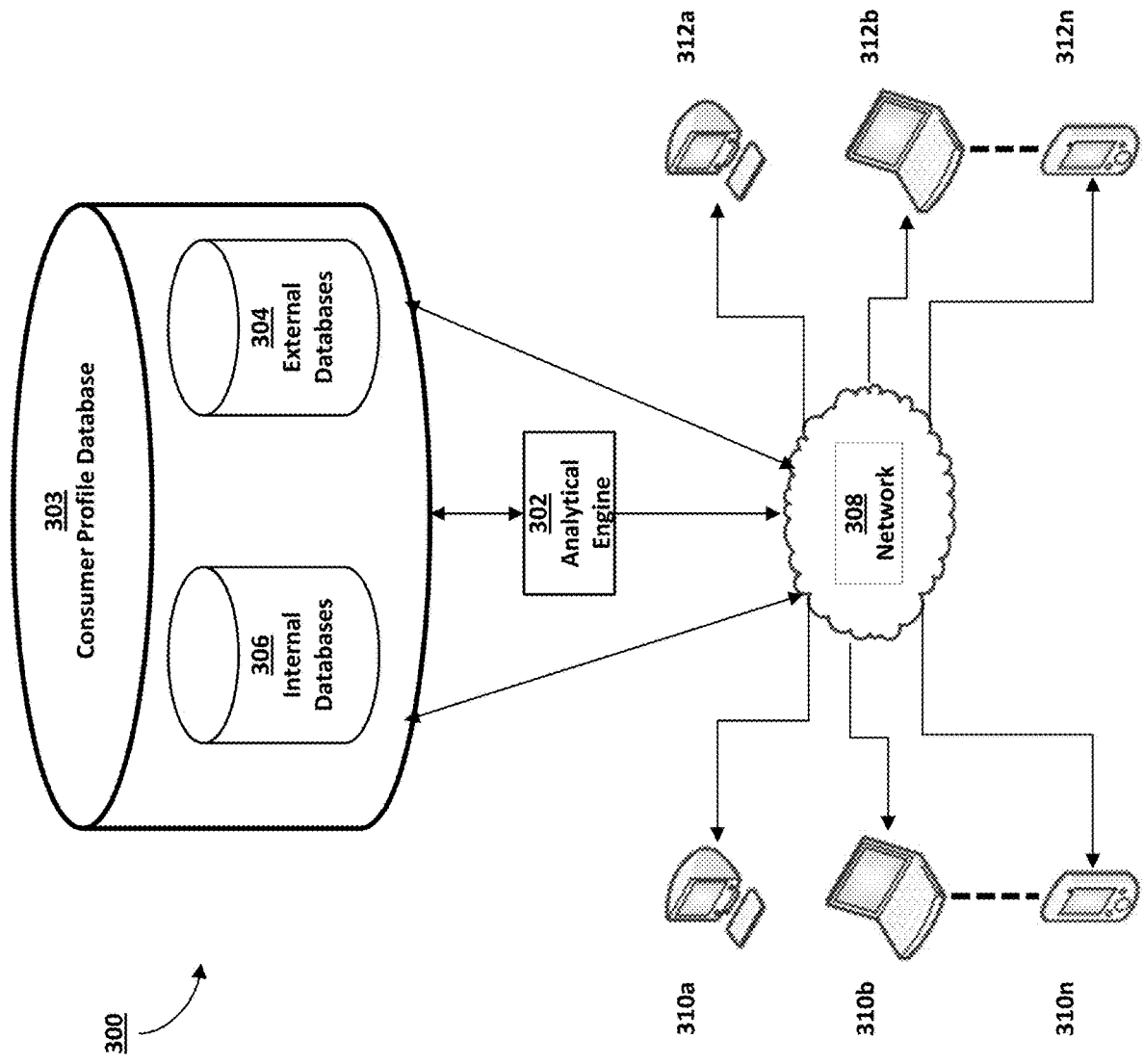
FIG. 3 is a block diagram illustrating a system including an analytical engine within a consumer assessment system, according to an embodiment.

FIG. 3 is a block diagram illustrating a consumer assessment and protection system including an analytical engine within a consumer protection company, according to an embodiment. The plurality of steps included in methods 100, 200a or 200b may be performed by one or more computing devices in the system described in 300. Each of the different components of consumer protection and consumer assessment system 300 may be implemented in any type of computer-based architecture including suitable processor-controlled devices that receive, process, and/or transmit digital data, configured as further described below and in FIG. 3. Examples of devices incorporating one or more suitable processor-controlled devices include smartphones, desktop computers, laptop computers, servers, tablets, PDAs, specialized computing platforms bioanalytic data processing, assessment algorithms, and the like.

Figure 4:
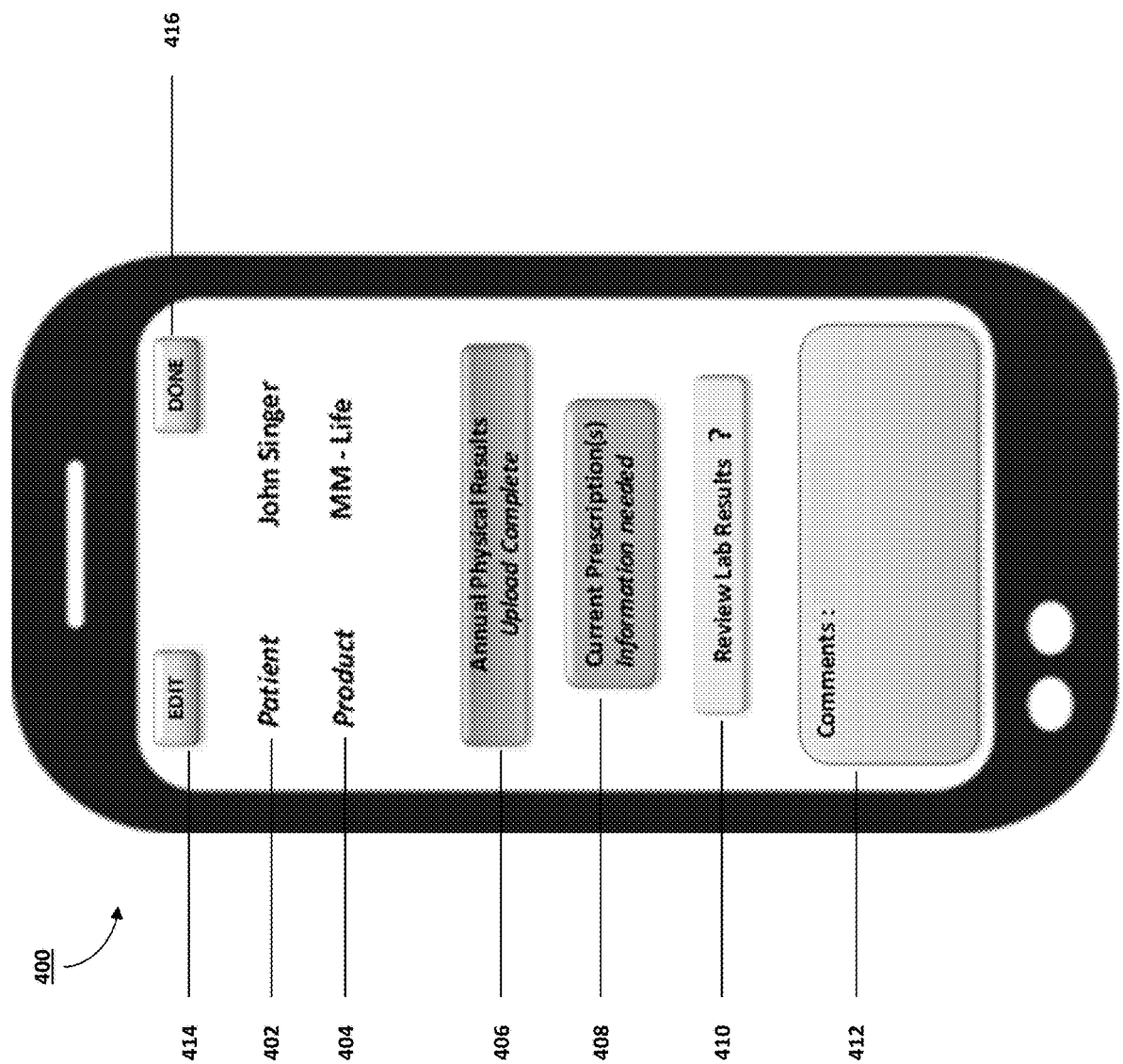
FIG. 4 is an exemplary illustration of a graphical user interface of a mobile application that can be presented on the consumer device or the physician device, according to an embodiment.

In FIG. 3, analytical engine 302 receives data from a consumer profile database 303, which contains external databases 304 and internal database 306 and is communicatively coupled to analytical engine 302. In these embodiments, analytical engine 302 processes the received data and stores the processed data at consumer profile database 303. In certain aspects, the consumer profile database 303, external databases 304, and internal databases 306 can be a single entity or nested databases or otherwise interconnected databases. The analytical engine 302 generates graphical user interface as shown in FIG. 4 at a physician device or consumer device or both, which facilitates the interaction with system 300 via a network 308. Graphical user interfaces are generated on consumer devices 310a-n that are used by the consumer and physician devices 312a-n that are used by the physician or his staff or other individuals authorized by the physician. Graphical user interfaces include one or more displays presented on a computing device that enable a user interaction with the analytical engine 302 or other devices in the system 302, associated data acquisition, and processing functionalities. These interfaces can be implemented within an operating system, a discrete GUI software layer, an application program, or any combination thereof.

In certain embodiments, analytical engine 302 can be implemented as software that runs on a server including a processing unit for running related algorithms or computer executable program instructions. The analytical engine 302 can be implemented using a single-processor system including one processor, or a multi-processor system including any number of suitable processors that may be employed to provide for parallel and/or sequential execution of one or more portions of the techniques described herein. Processes and logic flows described herein may be performed by one or more programmable processors executing one or more computer programs to perform functions by operating on input data and generating corresponding output. Processing unit may include a processor with computer-readable medium, such as a random access memory (RAM) (not shown) coupled to the processor. Examples of processor may include a microprocessor, application specific integrated circuit (ASIC), and field programmable object array (FPOA), among others.

In some embodiments, analytical engine 302 can be executed by a server, one or more server computers, a client computing device and the like. Examples of suitable implementations of the analytical engine 302 include servers, authorized client computing devices, smartphones, desktop computers, laptop computers, tablet computers, PDAs and other types of processor-controlled devices that receive, process, and/or transmit digital data. In an example, analytical engine 302 performs certain operations that are required for the proper operation of system architecture 300. Analytical engine 302 performs these operations as a result of central processing unit executing software instructions contained within a computer-readable medium, such as within memory. In one embodiment, the software instructions of the system are read into memory associated with the analytical engine 302 from another memory location, such as from storage device, or from another computing device via communication interface. In this embodiment, the software instructions contained within memory instruct the analytical engine 302 to perform processes that are described in FIGS. 1, 2a and 2b, above. Alternatively, hardwired circuitry may be used in place of or in combination with software instructions to implement the processes described herein. Thus, implementations described herein are not limited to any specific combinations of hardware circuitry and software.

The consumer profile database 303 is a body of information associated with the consumers and organized as records. The consumer profile database can comprise information from either external sources, internal sources, or both. In an embodiment, the consumer profile database comprises information records from both external databases 304 and internal database 306. In an embodiment, the consumer profile database is connected virtually or physically to external databases 304 and internal database 306. Information in these databases can be stored or retrieved dynamically using appropriate storage management software. Information stored in a consumer profile database specific to a particular consumer includes consumer name, motor vehicle records, physician records, hospital records, pharmaceutical records such as prescription drug databases, public records such as Social Security Death Index Master File, lifestyle details, behavior patterns, geographic information such as street address, zip code, travel patterns, and other medical and non-medical information. Information stored in a consumer profile database can also include purchasing history, previous consumer scores, viewed or purchased consumer protection products and services, and other financial information. One or more client-side and server-side technologies or combinations thereof can be implemented to ensure that the graphical user interfaces are dynamically generated based on the updates to the records in the consumer profile database. Content for personalized web-based or an app-based interfaces can be dynamically generated on consumer devices and physician devices, based on updates to the consumer profile database and plurality of inputs from the consumer devices and physician devices. Data communicated between the various devices, servers, and other components of the system is encrypted, stored, decrypted, and distributed using one or more firewalls, and/or file encryption protocols, and other encryption software.

In one or more embodiments, external databases 304 and internal databases 306 are implemented as relational databases that provide functions of fetching, indexing, and storing data. In these embodiments, internal databases 306 stores and provides aforementioned information as part of the consumer profile database and other stored data and files to one or more software modules within the consumer assessment system 300 for further analysis. Examples of data received from external databases 304 include motor vehicle records, pharmaceutical records such as prescription drug databases, public records such as Social Security Death Index Master File, and other databases to gather lifestyle, behavior, and other medical and non-medical information. External databases 304 and internal databases 306 may be implemented through database management systems (DBMS), such as, MySQL, PostgreSQL, SQLite, Microsoft SQL Server, Microsoft Access, Oracle, SAP, dBASE, FoxPro, IBM DB2, LibreOffice Base, FileMaker Pro, and/or any other type of database that may organize collections of data. In these embodiments, external databases 304 and internal databases 306 can be implemented using application protocols for accessing and maintaining distributed directory information services or data feeds such as, for example, Lightweight Directory Access Control (LDAP), among others. Data stored in fields of the databases can be updated as needed, for example, by a user with administrative access to the database to add new data to the libraries in the database as they become supported.

Different kinds of arrangements among consumer devices, physician devices, servers with the analytical engine, and consumer profile databases can be supported. In certain aspects, arrangements involve consumer devices, physician devices, and servers with the analytical engine can create connections to the consumer profile databases on demand, and keep them open when the application would otherwise close them. A pool of connections is thereby created. Thereafter, when the devices or servers require a new connection, it is supplied from the pool if one is available, or a new connection is created if not. It will be appreciated by those having skill in the art that data described herein as being stored in the databases can also be stored or maintained in non-transitory memory and accessed among subroutines, functions, modules, objects, program products, or processes, for example, according to objects and/or variables of such subroutines, functions, modules, objects, program products or processes. Any of the fields of the records, tables, libraries, and so on of the database can be multi-dimensional structures resembling an array or matrix and can include values or references to other fields, records, tables, or libraries. Any of the foregoing fields can contain either actual values or a link, a join, a reference, or a pointer to other local or remote sources for such values. External databases 304 can be, for example, a single database, multiple databases, or a virtual database, including data from multiple sources, for example, servers on the World Wide Web.

The network 308 may comprise any communication architecture, inclusive of devices and software, which facilitates communication between transmitter and receiver residing in one or more computing devices that form the system 300. It should also be obvious to one skilled in the art that the network components may be implemented in dedicated processing equipment, or alternatively in a cloud processing network. The network 308 may be the intranets, local area networks (LAN), cloud networks, virtual private networks (VPN), wireless area networks (WAN), and the internet, or any other network that enables servers and user devices to interact with one another. Non-limiting examples of devices comprising the network may include routers, switches, hubs, firewalls, proxy servers, telecommunications trunks, and the like. Accordingly, the communications network can be implemented, in whole or in part, over wireless communications network. In addition, according to various exemplary embodiments of the present invention, the wireless communications network can be implemented over any of various wireless communication technologies, for example: code division multiplexed access ("CDMA"), global system for mobile communications ("GSM"), and wireless local area network such as WiFi, World Interoperability for Microwave Access ("WiMAX"), or Bluetooth®.

The analytical engine 302 generates graphical user interfaces on computing devices, including consumer devices 310a-n and physician devices 312a-n. Such devices are communicatively coupled to and in bi-directional communication with other devices, databases, and components of the consumer assessment system 300. Computing devices, such as consumer devices 310a-n and physician devices 312a-n, can be a computer such as a laptop computer or a desktop computer, or a mobile computing device such as a smart phone, a cell phone, a tablet, a personal digital assistant (PDA), a mobile computer with a smart phone client, or any other data access-enabled device. The analytical engine 302 utilizes the graphical user interfaces to request, collect, and present information from and to one or more of the users, including the physician, the consumer, the agent. The users interact with the graphical user interface via an input/output (I/O) device such as, a touch screen or a mouse, a keyboard and/or a keypad working in concert with a display, and others. In some embodiments, data processing modules of the analytical engine 302 are further configured to automatically retrieve information requested by one or more consumer devices 310a-n and physician devices 312a-n and/or one or more software modules. In these embodiments, this information is obtained from external databases 304 and internal database 306. In other embodiments this information is obtained from the operation of one or more software modules within the consumer assessment system 300. The analytical engine 302 can include or be communicatively coupled to one or more software modules, including but not limited to one or more consumer assessment modules, quoting modules, alert and notification modules, document management modules, and administration modules. In one or more embodiments, the analytical engine 302 can interact with external services, applications, and databases through one or more application programming interfaces ("API"), an RSS feed, or some other structured format. The API can be any Representational State Transfer Application Programming Interface (REST API) that controls and manages one or more APIs. In these embodiments, API provides web services to one or more mobile applications installed on the computing devices. Examples of web services include showing data on a website, uploading large amounts of data that will later be consumed by a mobile app, downloading data to run custom analytics, exporting data, and the like.

Mobile applications of the consumer assessment process can be implemented as software that can be downloaded and installed on computing devices 310a-n that are used by the consumer and computing devices 312a-n that are used by the physician, for interacting with the system such as 300 of a consumer protection company. Examples of mobile application are GUI applications that may be available at, downloaded, and installed from a public software app stores or digital application distribution platforms, such as Apple iTunes®, Google Play® Store and Amazon.com®, among others. In these embodiments, mobile application includes the following exemplary functions: allowing the user to create and manage a user account in the consumer protection company's system; allowing the user to see the available consumer protection products, allowing the user to receive communications such as e-mails or text messages from the consumer protection system 300; and allowing the user to see updates as the application for the consumer protection product is processed through the system to ultimate decision, such as issuance of consumer protection product, or denial, or presentation of other products.

The mobile application can have a landing graphical user interface or an introductory interface where the user is introduced to the consumer protection company, or its products and services, or combinations of this information. Upon entering proper credentials, the user is presented with graphical user interfaces that present, collect, and communicate information about a consumer and the consumer protection products and services under consideration.

FIG. 4 is an exemplary illustration of a graphical user interface of a mobile application implementing certain aspects of the processes that are described in FIGS. 1 and 2, above. In FIG. 4, graphical user interface 400 presented at one or more of consumer devices 310a-n and physician devices 312a-n includes certain information such as name of the consumer or patient 402 and particular consumer protection product 404 under consideration. Then the graphical user interface provides a series of clickable buttons that are configured to enable the user to provide information to the consumer protection company. These buttons serve as links or provide a reference to records stored in the consumer profile database. A person skilled in the relevant art will appreciate that the graphical user interface depicted in this embodiment, may be generated by the analytical server and transmitted to the mobile device. For example, the analytical server may generate an instruction configured to display all the buttons (displayed below) and transmit such instruction to the mobile device. The analytical server may also receive all data generated from the physician or the consumer interacting with the graphical user interface and instruct further actions/displays. In FIG. 4, a clickable button 406 permits the user to upload annual physical results to the consumer protection company for evaluation, and this can be performed by either the physician directly using the physician device or by the consumer using the consumer device after acquiring the results from the physician. This button 406 can be color-coded, for example in green, to indicate that this information has been already provided to the consumer profile database. A clickable button 408 permits the user to upload current prescription information to the consumer profile database, and further for processing by the analytical engine, and this upload can be performed by either the physician using the physician device or by the consumer using the consumer device after acquiring the results from the physician. This button 408 can be color-coded, for example in red, to indicate that this information has not been provided to the consumer profile database. A clickable button 410 permits the user to upload information regarding results from the lab, such as bioanalytic information, to the consumer profile database, and further for processing by the analytical engine, and this can be performed by either the physician directly or the consumer after acquiring the results from the physician. This button 410 can be color-coded, for example in yellow, to indicate that this information has not been provided to the consumer profile database, and requires further review. Further review can be indicative of missing data, or erroneous data, or other issues with the information from the lab, the physician device, or the consumer profile database. Comment boxes 412 can also be provided to permit the users to include information that is not otherwise captured in the forms, which are uploaded or provided to the consumer profile database, and further for processing by the analytical engine. Shown herein are a few commonly used controls such as a button 414 to edit the information provided through the interface and a button 416 to indicate that the user is done with the session for now. Not shown herein are a number of commonly used controls, such as controls that are used to maximize, minimize, resize, and close graphical user interface 400. Graphical user interfaces can also include other controls such as scrollbars and navigational controls (not shown). Navigation controls allow a user to toggle between different graphical user interfaces of the mobile application, such as from the graphical user interface shown in FIG. 4 to other interfaces, for example one that allows the user to manage his own user information such as username, profile image, and other user information such as biographical, professional, work-related, and other lifestyle-related information. It should be understood that mobile application can include less fields, more fields, or different fields on the graphical user interface depending on the desired goals of the consumer protection company. The mobile application can also provide one or more interfaces with one or more icons, screen layouts, and other visual and verbal cues to communicate with the user.

The mobile application can present (e.g., the analytical engine may instruct the mobile application to display) the user with graphical user interfaces that permit the user to search the categories of consumer protection products and services offered by the consumer protection company, including the types of consumer protection products available within a specific category. Graphical user interfaces are generated that display the consumer protection products and services in rank order that match a search request from the user. In those embodiments, the analytical engine may rank the consumer protection products and generate an instruction to display the products based on their respective ranking. Other functionalities can include functionalities to facilitate communication among the various parties involved in the consumer protection process, such as agents, physicians, and the consumer.

Certain embodiments of the graphical user interface of the mobile application allow a user to create an account within the system of the consumer protection company. In these embodiments, the API running on the analytical engine receives an account request including all personal data of the consumer who wishes to open an account. The API processes the information and creates an account within the system of the consumer protection company. Examples of personal data include name, emails, phone numbers, lifestyle information, work-related information, demographical information, and the like.

Embodiments disclosed herein provide consumer assessment, such as independent assessment of input from non-physician medical professionals, such as paramed data. In certain embodiments, multiple levels of consumer assessment may be offered, wherein each of the different levels of consumer assessment may collect or require a different amount of information from the consumer. As an example, in cases where there is no collection of data using non-physician medical professionals, such as paramed data, an adjusted consumer protection may be offered.

As a result of using biological information, such as values of the biological parameters of consumers, directly from physicians for consumer assessment purposes, the invasive collection of paramed data by visiting individuals at homes or offices or other personal spaces may be reduced or eliminated, which may significantly reduce privacy concerns of consumers who avoid obtaining consumer protection products and services, and increase the number of consumers for such products and services. Similar benefits can exist when the embodiments disclosed herein are applied to life, health or other consumer product programs.

The foregoing method descriptions and the process flow diagrams are provided merely as illustrative examples and are not intended to require or imply that the steps of the various embodiments must be performed in the order presented. As will be appreciated by one of skill in the art the steps in the foregoing embodiments may be performed in any order. Words such as "then," "next," etc. are not intended to limit the order of the steps; these words are simply used to guide the reader through the description of the methods. Although process flow diagrams may describe the operations as a sequential process, many of the operations may be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

The various illustrative logical blocks, modules, circuits, and algorithm steps described in connection with the embodiments disclosed here may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the invention. Thus, the operation and behavior of the systems and methods were described without reference to the specific software code being understood that software and control hardware can be designed to implement the systems and methods based on the description here.

When implemented in software, the functions may be stored as one or more instructions or code on a non-transitory computer-readable or processor-readable storage medium. The steps of a method or algorithm disclosed here may be embodied in a processor-executable software module which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used here, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

When implemented in hardware, the functionality may be implemented within circuitry of a wireless signal processing circuit that may be suitable for use in a wireless receiver or mobile device. Such a wireless signal processing circuit may include circuits for accomplishing the signal measuring and calculating steps described in the various embodiments.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

Any reference to claim elements in the singular, for example, using the articles "a," "an" or "the," is not to be construed as limiting the element to the singular. The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A method comprising:
receiving, by a server, a consumer token associated with an electronic consumer device, wherein the consumer token comprises a string of characters uniquely identifying a consumer operating the electronic consumer device;
in response to the consumer token being associated with a first data record of the consumer stored in a consumer profile database, generating by the server, a first graphical user interface comprising a first plurality of questions to be displayed on the electronic consumer device;
upon transmitting the first graphical user interface to the electronic consumer device, receiving by the server, a first plurality of inputs corresponding to the first plurality of questions;
receiving, by the server, a session request from the electronic consumer device;
generating, by the server, a session token comprising a string of characters uniquely identifying a physician and a code associated with a predetermined time interval during which consumer data is received from an electronic physician device operated by the physician;
generating, by the server, a first instruction configured to cause the electronic consumer device to display the time interval and data associated with the physician;
upon transmitting the first instruction to the electronic consumer device, receiving by the server, a physician token associated with the electronic physician device, wherein the physician token comprises a string of characters uniquely identifying the physician;
upon the server determining that the physician token is associated with the consumer token and the session token and a time of receipt of the physician token is within the predetermined time interval, initiating, by the server, a secure communication session with the electronic physician device configured to be active only during the predetermined time interval associated with the session token;
while the secure communication session is active, generating, by the server, a second graphical user interface comprising a second plurality of questions to be displayed on the electronic physician device, wherein the second plurality of questions correspond to biological parameters associated with the consumer;
upon transmitting the second graphical user interface to the electronic physician device, receiving by the server within the predetermined time interval, a second plurality of inputs corresponding to the second plurality of questions;

receiving, by the server, a specimen identifier corresponding to a physical sample acquired from the consumer;

linking, by the server, the specimen identifier, the physician identifier, the consumer identifier, and the session identifier;

receiving, by the server from the electronic physician device, data associated with the physical sample;

generating, by the server, a consumer score based on a plurality of values associated with each of the first and the second plurality of inputs and the data associated with the physical sample;

generating, by the server, a second data record of the consumer in the consumer profile database based on processing of the consumer score, wherein the second data record is associated with a consumer protection product for the consumer;

generating, by the server, a second instruction configured to display the second data record of the consumer; and transmitting, by the server, the second instruction to at least one of the electronic consumer device or the electronic physician device.

2. The method of claim 1, further comprising:
generating, by the server, a mobile application configured to receive the first plurality of inputs, the second plurality of inputs, and the data associated with the physical sample and transmit the first plurality of inputs and the second plurality of inputs to the consumer profile database.

3. The method of claim 1, further comprising:
generating, by the server, a web page-based interface configured to receive the first plurality of inputs, the second plurality of inputs, and the data associated with the physical sample and transmit the first plurality of inputs and the second plurality of inputs to the consumer profile database.

4. The method of claim 1, further comprising:
generating, by the server, a third graphical user interface configured to display the consumer protection product; and transmitting, by the server, the third graphical user interface to the consumer device.

5. The method of claim 1, wherein the consumer protection product is a health-related product.

6. The method of claim 1, further comprising:
receiving, by the server, the data associated with the physical sample from the consumer during the time interval associated with the session token.

7. The method of claim 6, wherein the second plurality of inputs corresponding to consumer's biological parameters is received, by the server, from the physician device responsive to processing the physical sample.

8. The method of claim 1, wherein the biological parameters comprise one or more biometric parameters.

9. The method of claim 1, wherein the biological parameters comprises one or more bioanalytic parameters.

10. A computer system comprising:
an electronic consumer device;
an electronic physician device; and
a server configured to:
receive a consumer token associated with the electronic consumer device, wherein the consumer token comprises a string of characters uniquely identifying a consumer;

in response to the consumer token being associated with a first data record of the consumer stored in a consumer profile database, generate a first graphical user interface comprising a first plurality of questions to be displayed on the electronic consumer device;

upon transmitting the first graphical user interface to the electronic consumer device, receive a first plurality of inputs corresponding to the first plurality of questions;

receive a session request from the electronic consumer device;

generate a session token comprising a string of characters uniquely identifying a physician and a code associated with a predetermined time interval for consumer data received from the electronic physician device;

generate a first instruction configured to display the time interval and data associated with the physician;

upon transmitting the first instruction to the electronic consumer device, receive a physician token associated with the electronic physician device wherein the physician token comprises a string of characters uniquely identifying the physician;

upon the server determining that the physician token is associated with the customer token and a time of receipt of the physician token is within the predetermined time interval, initiate a secure communication session with the electronic physician device, wherein the secure communication session is configured to be active only during the predetermined time interval associated with the session token;

while the secure communication session is active, generate a second graphical user interface comprising a second plurality of questions to be displayed on the electronic physician device, wherein the second plurality of questions correspond to biological parameters associated with the consumer;

upon transmitting the second graphical user interface to the electronic physician device, receive within the predetermined time interval a second plurality of inputs corresponding to the second plurality of questions;

receive a specimen identifier corresponding to a physical sample acquired from the consumer;

link the specimen identifier, the physician identifier, the consumer identifier, and the session identifier;

receive, from the electronic physician device, data associated with the physical sample;

generate a consumer score based on a plurality of values associated with each of the first and the second plurality of inputs and the data associated with the physical sample;

generate a second record of the consumer in the consumer profile database based on processing of the consumer score, wherein the second data record is associated with a consumer protection product for the consumer;

generate a second instruction configured to display the second data record of the consumer; and transmit the second instruction to at least one of the electronic consumer device and the electronic physician device.

11. The computer system of claim 10, wherein the server is further configured to:
generate a mobile application configured to receive the first plurality of inputs and the second plurality of inputs and transmit the first plurality of inputs, the second plurality of inputs, and the data associated with the physical sample to the consumer profile database.

12. The computer system of claim 10, wherein the server is further configured to:
   generate a web page-based interface configured to receive the first plurality of inputs and the second plurality of inputs and transmit the first plurality of inputs, the second plurality of inputs, and the data associated with the physical sample to the consumer profile database.

13. The computer system of claim 10, wherein the server is further configured to:
   generate a third graphical user interface configured to display the consumer protection product; and
   transmit the third graphical user interface to the consumer device.

14. The computer system of claim 10, wherein the consumer protection product is a health-related product.

15. The computer system of claim 10, wherein the server is further configured to:
   receive the data associated with the physical sample from the consumer during the time interval associated with the session token.

16. The computer system of claim 15, wherein the second plurality of inputs corresponding to consumer's biological parameters is receive from the physician device responsive to processing the physical sample.

17. The computer system of claim 10, wherein the biological parameters comprise one or more biometric parameters.

18. The computer system of claim 10, wherein the biological parameters comprises one or more bioanalytic parameters.

* * * * *